United States Patent [19]

Toth-Sarudy et al.

[11] 4,418,205

[45] Nov. 29, 1983

[54] 16-AMINO-18,19,20-TRINOR-PROSTAGLANDIN DERIVATIVES, AND ACID ADDITION SALTS

[75] Inventors: Eva Toth-Sarudy; Gabor Ambrus; György Cseh; Janos Borvendeg; Imre Moravcsik; Gabriella Mezeyi, all of Budapest, Hungary

[73] Assignee: Patentbureau Danubia, Budapest, Hungary

[21] Appl. No.: 329,039

[22] Filed: Dec. 9, 1981

[30] Foreign Application Priority Data

Dec. 9, 1980 [HU] Hungary ............................ 2941/80

[51] Int. Cl.$^3$ .......................................... C07C 177/00
[52] U.S. Cl. ..................................... 560/39; 562/444; 424/309
[58] Field of Search .................... 560/39, 42; 562/444; 424/309

[56] References Cited

PUBLICATIONS

Derwent Abstract 38572A/22, BE 863-116, 01-20-78.
Derwent Abstract 94831X/51, J5 1125-046, 11-22-74.
Derwent Abstract 13442W/08, J4 9109-341, 02-26-73.
Derwent Abstract 26295W/16, FR 2235-927, 06-25-73.

*Primary Examiner*—Paul J. Killos
*Attorney, Agent, or Firm*—Keil & Witherspoon

[57] ABSTRACT

The invention relates to new 16-amino-18,19,20-trinor-prostaglandin derivatives of general formula I, having at C-17 a substituted or unsubstituted phenyl group, wherein C-15 and C-16 may have either S or R configuration, Y stands for a hydrogen atom or a lower alkyl group, W stands for a hydrogen atom, halogen atom, hydroxy group, lower alkyl or alkoxy group, and their acid addition salts. These compounds can be prepared by removing the ester group and the p-nitrobenzyloxycarbonyl protective group of a 9α,11α,15-trihydroxy-16-p-nitrobenzyloxycarbonylamido-17-phenyl-5-cis,13-trans-18,19,20-trinor-prostadienoic acid derivative of general formula XII—wherein C-15 and C-16 may have either S or R configuration, W is as defined above, and Y stands for a lower alkyl group—in an optional sequence with the limitation that in those compounds of general formula I where W is as defined above and Y stands for a lower alkyl group, solely the p-nitrobenzyloxycarbonyl group is removed, and the resulting product of general formula I is optionally converted with an organic or inorganic acid into a salt.

The new prostaglandin derivatives of the invention have valuable therapeutical properties, and can be applied in cattle raising for estrus and birth synchronization, furthermore in the veterinary praxis for the treatment of sterility, chronic endometritis and pyometry.

11 Claims, No Drawings

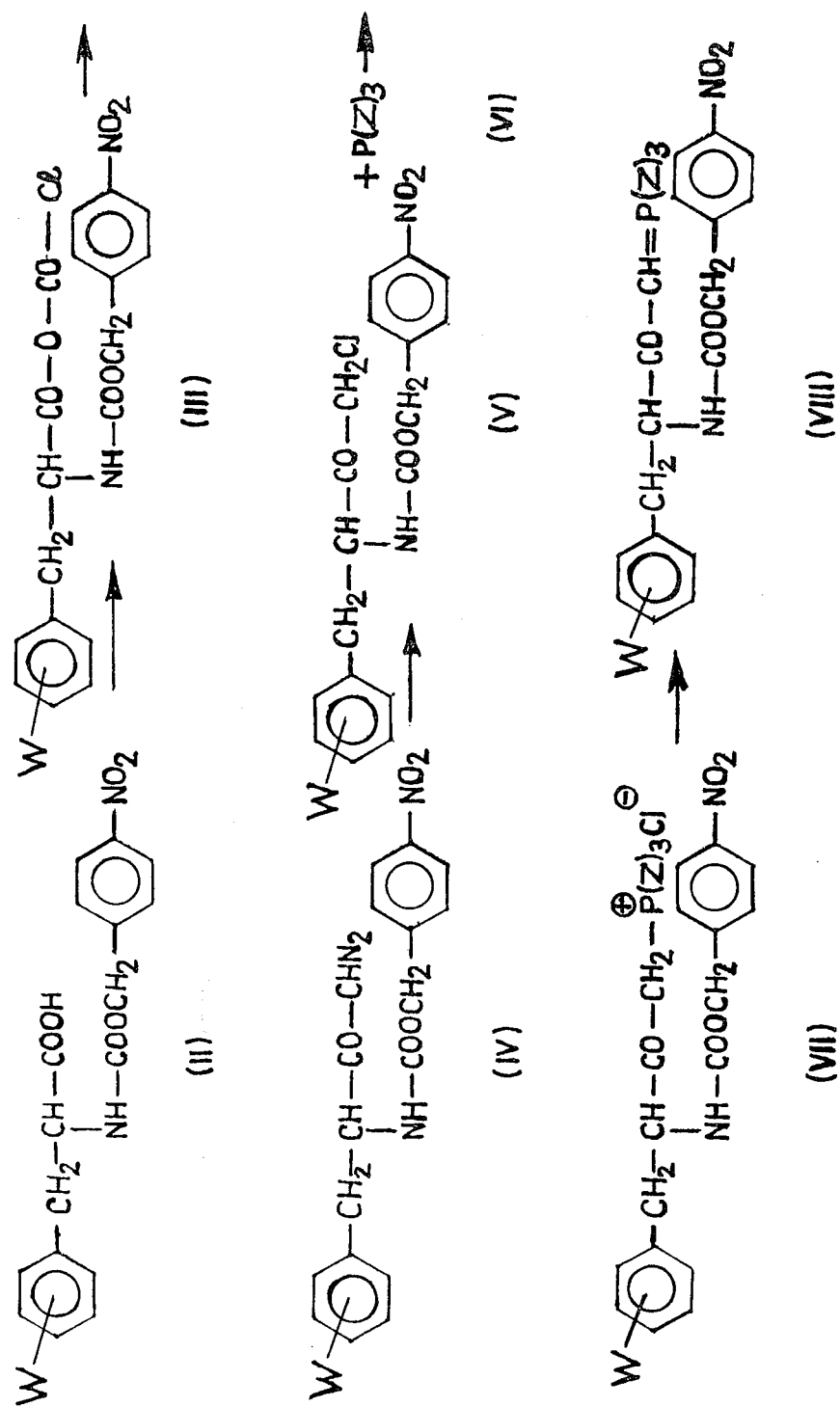

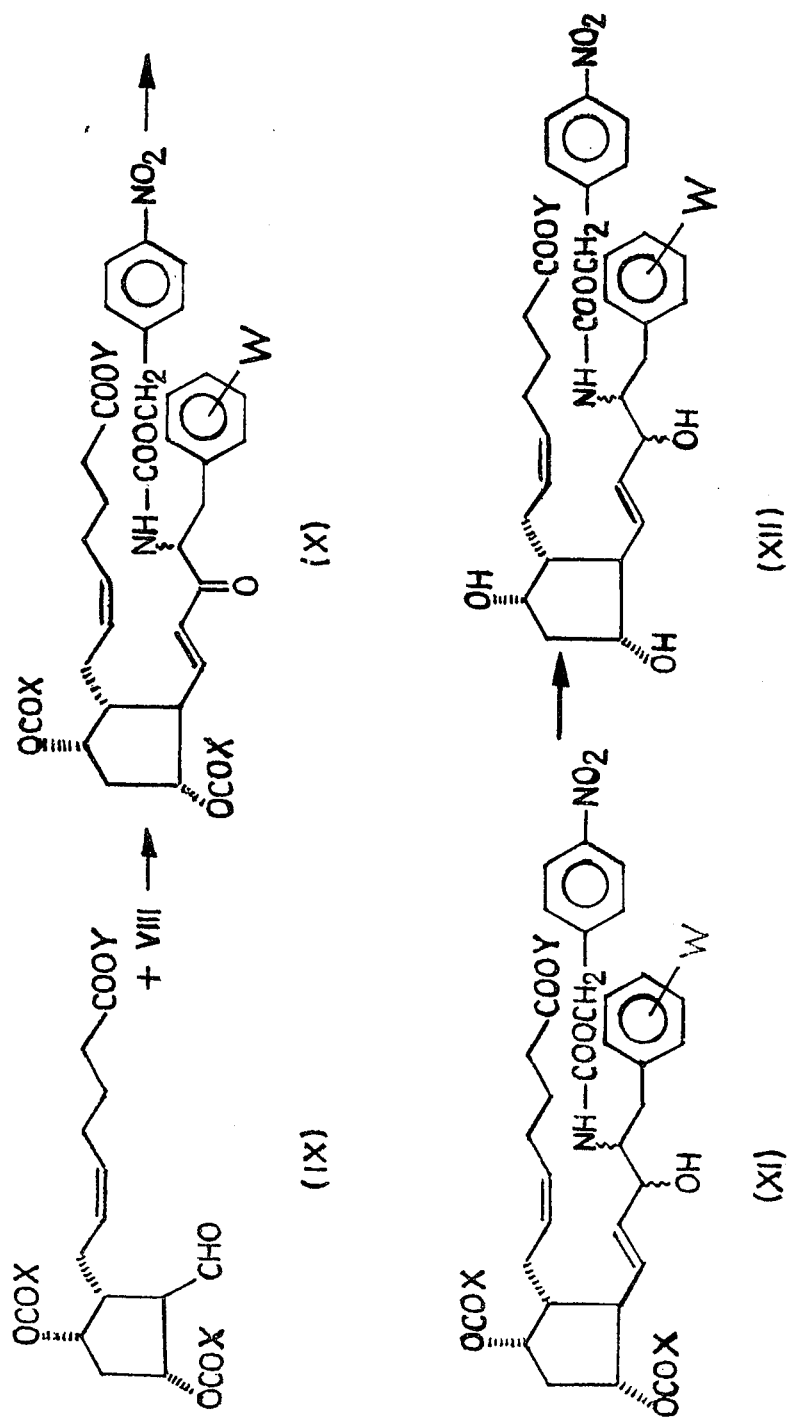

16-AMINO-18,19,20-TRINOR-PROSTAGLANDIN DERIVATIVES, AND ACID ADDITION SALTS

The invention relates to new 16-amino-18,19,20-trinor-prostaglandin derivatives of general formula I

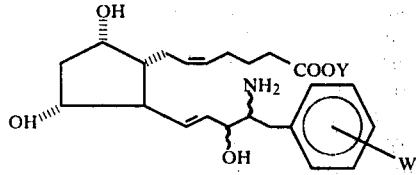

having at C-17 a substituted or unsubstituted phenyl group, wherein C-15 and C-16 may have either S or R configuration, Y stands for a hydrogen atom or a lower alkyl group, W for a hydrogen atom, halogen atom, hydroxy group, lower alkyl or alkoxy group, and their acid addition salts. Furthermore, the invention relates to a process for the preparation of these compounds.

Drug research aims to utilize the physiological activity of prostaglandins in diverse fields of therapy. Natural prostaglandins possess the unfavourable property of exhibiting simultaneously a wide range of activity, furthermore they are rapidly decomposed by the organisms. These disadvantages may be eliminated by preparing prostaglandin analogues which are metabolized at a lower rate, and which possess a more selective activity /P. Ramwell and I. Saw: Ann. N.Y. Acad. Sci. 180, 10 /1971//.

The invention relates to novel prostaglandin derivatives which have a 1-amino-2-phenyl-ethyl group optionally substituted by a halogen, hydroxy, alkyl or alkoxy group, instead of the n-amyl group forming the C-16 to C-20 fragment of natural prostaglandins, and a process for the preparation thereof.

Within the organism there are several phenyl-ethyl derivatives of physiological importance /for instance phenylalanine, tyrosine, L-dopa/, furthermore several drugs /for instance various sympathomimetic agents/ belong to this family of compounds. Consequently, it was assumed that the physiological properties of natural prostaglandins might be modified by introducing a phenyl-ethylamine group in the side chain of prostaglandins.

In compliance with the invention the new 16-amino-18,19,20-trinor-prostaglandin derivatives of general formula I, having at C-17 a substituted or unsubstituted phenyl group, wherein C-15 and C-16 may have either S or R configuration, Y stands for a hydrogen atom or a lower alkyl group, W for a hydrogen atom, halogen atom, hydroxy group, lower alkyl or alkoxy group, and their acid addition salts, can be prepared by removing the ester group and the p-nitrobenzyloxycarbonyl protective group of a 9α,11α,15-trihydroxy-16-p-nitrobenzyloxycarbonylamido-17-phenyl-5-cis,13-trans-18,19,20-trinor-prostadienoic acid derivative of the general formula XII

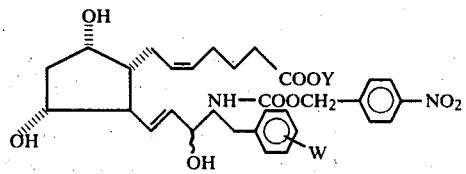

wherein C-15 and C-16 may have either S or R configuration, W is specified as above, and Y stands for a lower alkyl group, in an optional sequence, with the limitation that in those compounds of general formula I where W is as defined above and Y stand for a lower alkyl group, solely the p-nitrobenzyloxycarbonyl group is removed, and the resulting product of general formula I is optionally converted with an organic or inorganic acid into a salt.

According to a preferred method of the invention the p-nitrobenzyloxycarbonyl group of a 9α,11α,15-trihydroxy-16-p-nitrobenzyloxycarbonyl-amido-17-phenyl-5-cis,13-trans-18,19,20-trinor-prostadienoic acid derivative of general formula XII—wherein C-15 and C16 may have either S or R configuration, and Y and W have the same meaning as above—is removed in acetic acid with Zn dust, and the ester group of the resulting 9α,11α,15-trihydroxy-16-amino-17-phenyl-5-cis,13-trans-18,19,20-trinor-prostadienoic acid ester is optionally hydrolyzed in a mixture of water and a lower alkanol, preferably methanol, with an alkali metal hydroxide, preferably lithium hydroxide, and treated with an acid until reaching the isoelectric point of the product. The isolated product can be converted into an acid addition salt by methods known per se. The Zn dust reduction in acetic acid is carried out within a temperature range of $-5°$ C. to $+10°$ C., preferably at $0°$ C., the ester hydrolysis between $0°$ C. to $+10°$ C., preferably at $+5°$ C.

According to an other preferred method of the invention the p-nitrobenzyloxycarbonyl protective group of a compound of general formula XII can be removed by catalytic transfer hydrogenation in the presence of a PD-C catalyst and cyclohexadiene.

The ester hydrolysis can advantageously be carried out by means of esterase enzymes such as Rhizopus orizae lipase /Hungarian Patent No. 160,109/. In the course of the process of the invention the sequence of the removal of the p-nitrobenzyloxycarbonyl protective group and the ester group may be interchanged.

For preparing the acid addiction salts of the compounds of general formula I, a compound of general formula I, possessing a free amino group, and obtained by the removal of the p-nitrobenzyloxycarbonyl protective group, and optionally by the cleavage of the ester group, is preferably reacted in solution with an inorganic or organic acid, or eventually with the solution thereof in a suitable solvent, and the acid addition salt formed is separated by methods known per se.

Compounds of general formula XII serving as starting materials of the process of the invention are also new. They can be synthesized in the following preferred way:

A 1-carboxy-1-p-nitrobenzyloxycarbonyl-amido-2-phenyl-ethane derivative of general formula II—wherein W stands for a hydrogen atom, halogen atom, hydroxy, alkyl or alkoxy group—is reacted with chloroformic acid alkyl ester, the resulting mixed anhydride derivative of formula III is converted with diazomethane to the 1-diazo-2-oxo-3-p-nitrobenzyloxycarbonylamido-4-phenyl-butane derivative of formula IV—wherein W has the same meaning as above. This is treated with hydrochloric acid, the resulting 1-chloro-2-oxo-3-p-nitrobenzyloxycarbonylamido-4-phenyl-butane derivative of formula V—wherein W has the same meaning as above—is reacted with a trisubstituted phosphine of general formula VI—wherein Z stands for an alkyl or aryl group—and the resulting phosphonium chloride derivative of formula VII—wherein W and Z have the same meaning as above—is treated with an alkali metal hydroxide. The obtained phosphorane derivative of formula VIII—wherein W and Z have the same meaning as above—is reacted with the $1\alpha$-/6-carbalkoxy-2-hexenyl/-$2\beta$-formyl-cyclopentane-$3\alpha,5\alpha$-diol-diacylate of general formula IX—wherein X stands for a lower alkyl or aryl group, and Y for a lower alkyl group. The resulting $9\alpha,11\alpha$-diacyloxy-15-oxo-16-p-nitrobenzyloxycarbonylamido-17-phenyl-5-cis,13-trans-18,19,20-trinor-prostandienoic acid alkyl ester derivative of general formula X—wherein C-16 may have either S or R configuration, furthermore W, X and Y have the same meaning as above—is reduced by an alkali metal borohydride. The reduction products of general formula XI, namely the $9\alpha,11\alpha$-diacyloxy-15/S/-hydroxy-16-p-nitrobenzyloxycarbonylamido-17-phenyl-5-cis,13-trans-18,19,20-trinor-prostadienoic acid alkyl ester and $9\alpha,11\alpha$-diacyloxy-15/R/-hydroxy-16-p-nitrobenzyloxycarbonylamido-17-phenyl-5-cis,13-trans-18,19,20-trinor-prostadienoic acid alkyl ester derivatives—wherein W, X and Y have the same meaning as above—are separated and subsequently hydrolyzed in methanolic solution with p-toluenesulfonic acid.

In the synthesis of compounds serving as starting materials in the process of the invention and having general formula XII it is preferred to use optically active $1\alpha$-/6-carbalkoxy-2-hexenyl/-$2\beta$-formyl-cyclopentane-$3\alpha,5\alpha$-diol-diacylate derivatives as key-compounds.

Starting from the known /-/$3\alpha,5\alpha$-dihydroxy-$2\beta$-/trityloxymethyl/-cyclopentane-$1\alpha$-acetic acid γ-lactone /Tetrahedron Letters, 4639 /1976// these compounds can advantageously be prepared in the following way:

The $3\alpha,5\alpha$-dihydroxy-$2\beta$-/trityloxymethyl/-cyclopentan-$1\alpha$-acetic acid γ-lactone is reduced by diisobutyl-aluminium-hydride, the resulting $3\alpha,5\alpha$-dihydroxy-$2\beta$-/trityloxymethyl/-cyclopentan-$1\alpha$-acetaldehyde γ lactol is reacted with 4-carboxybutylidene-triphenyl-phosphorane, the obtained $1\alpha$-/6-carboxy-2-hexenyl/-$2\beta$-/trityloxymethyl/-cyclopentane-$3\alpha,5\alpha$-diol is esterified, the resulting $1\alpha$-/6-carbalkoxy-2-hexenyl/-$2\beta$-/trityloxymethyl/-cyclopentane-$3\alpha,5\alpha$-diol is acylated with an acid chloride or acid anhydride, prepared from an aliphatic or aromatic carboxylic acid, giving $1\alpha$-/6-carbalkoxy-2-hexenyl/-$2\beta$-/trityloxymethyl/-cyclopentane-$3\alpha,5\alpha$-diol-diacylate. This is treated with an organic or inorganic acid, and finally the obtained $1\alpha$-/6-carbalkoxy-2-hexenyl/-$2\beta$-hydroxymethyl-cyclopentane-$3\alpha,5\alpha$-diol-diacylate is submitted to oxidation /Hungarian Patent Specification No. 177,834.

The $1\alpha$-/6-carbalkoxy-2-hexenyl/-$2\beta$-formyl-cyclopentane-$3\alpha,5\alpha$-diol-diacylates are preferred starting materials for preparing prostaglandin derivatives modified in their 3-hydroxy-1-trans-octenyl side chain, as these intermediary substances, being in the final stage of prostaglandin synthesis can be easily converted into various prostaglandin analogues by suitably varying the Wittig-reagent utilized for side-chain formation.

The Wittig-reagents required for preparing the prostaglandin derivatives of the present invention can be prepared from either S- or R-phenylalanine, or from phenylalanine derivatives substituted by a halogen atom, hydroxy, alkyl or alkoxy group in the benzene nucleus according to the following reaction scheme:

In the course of the synthesis of $9\alpha,11\alpha,15/\xi/$-trihydroxy-16/S/-amino-17-phenyl-5-cis,13-trans-18,19,20-trinor-prostadienoic acids /I, Y=W=H/ first S-phenylalanine is converted into its p-nitrobenzyloxycarbonyl derivative by a known method /D. T. Gish and F. H. Carpenter: J. Am. Chem. Soc. 75, 950 /1953//. The p-nitrobenzyloxycarbonyl group is the preferred protective group of the amino group, as it can be easily removed by reduction with zinc in acetic acid at 0° C. At these conditions the PGF-type 16-amino-17-phenyl-18,19,20-trinor-prostaglandin derivatives are rather stable, and are not decomposed.

The p-nitrobenzyloxycarbonyl-S-phenylalanine is transformed in tetrahydrofuran, in the presence of N-methylmorpholine by the addition of a molar amount of isobutyl chloroformate at $-15°$ C. into a mixed anhydride derivative. In the course of the reaction the N-methylmorpholine hydrochloride is precipitated. An excess of a solution of diazomethane in ether is added dropwise to this precipitated mixture, and stirred for 3 hours at $-15°$ C. Then dry hydrogen chloride is led into the mixture containing the diazoketone derivative, formed upon the reaction with diazomethane, at $-15°$ C. to obtain the 1-chloro-2-oxo-3/S/-p-nitrobenzyloxycarbonylamido-4-phenyl-butane.

The 1-chloro-2-oxo-3/S/-p-nitrobenzyloxycarbonylamido-4-phenyl-butane is reacted in ether at boiling temperature with tri-n-butyl-phosphine or triphenyl-phosphine, resp. The phosphorane derivatives, utilized as Wittig reagents, are set free from the resulting phosphonium salts by the addition of the solution of an alkali metal hydroxide.

The $1\alpha$-/6-carbalkoxy-2-hexenyl/-$2\beta$-formylcyclopentane-$3\alpha,5\alpha$-diol-diacylates are reacted in ether for 8 to 10 hours with 2 moles of tri-n-butyl-2-oxo-3/S/-p-nitrobenzyloxycarbonylamido-4-phenyl-butylidene-phosphorane. The $9\alpha,11\alpha$-diacyloxy-15-oxo-16/S/-p-nitrobenzyloxycarbonylamido-17-phenyl-5-cis,13-trans-18,19,20-trinor-prostandienoic acid alkyl ester derivative, formed in the course of the reaction, is separated from the tri-n-butyl-phosphine oxide, also formed in the reaction, and from the residual excess of tri-n-butyl-2-oxo-3/S/-p-nitrobenzyloxycarbonylamido-4-phenyl-butylidene-phosphorane preferably by chromatography carried out on a silica gel column.

Reducing the $9\alpha,11\alpha$-diacyloxy-15-oxo-16/S/-p-nitrobenzyloxycarbonylamido-17-phenyl-5-cis,13-trans-18,19,20-trinor-prostadienoic acid alkyl ester derivative with an alkali metal borohydride, i.e. sodium borohydride, a mixture of $9\alpha,11\alpha$-diacyloxy-15/S/-hydroxy-16/S/-p-nitrobenzyloxycarbonylamido-17-phenyl-5-cis,13-trans-18,19,20-trinor-prostadienoic acid alkyl ester and $9\alpha,11\alpha$-diacyloxy-15/R/-hydroxy-16/S/-p-nitrobenzyloxycarbonylamido-17-phenyl-5-cis,13-trans-18,19,20-trinor-prostadienoic acid alkyl ester derivatives are formed. They differ from each other in the configuration of C-15. The two diastereomers can preferably be separated by preparative thin-layer chromatography or column chromatography.

At the separation carried out on silica gel thin-layers in a developing solvent mixture of n-heptane-ethyl acetate 1:1, the polar product was designated isomer A, and the apolar one isomer B, as the configuration of C-15 in the two diastereomers is not elucidated yet.

Hydrolyzing the 9α,11α-diacyloxy-15/ξ/-hydroxy-16/S/-p-nitrobenzyloxycarbonylamido-17-phenyl-5-cis,13-trans-18,19,20-trinor-prostadienoic acid alkyl ester /isomer A/ and the 9α,11α-diacyloxy-15/ξ/-hydroxy-16/S/-p-nitrobenzyloxycarbonylamido-17-phenyl-5-cis,13-trans-18,19,20-prostadienoic acid alkyl ester /isomer B/ derivatives in methanolic solution with p-toluenesulfonic acid at room temperature, 9α,11α,15/ξ/-trihydroxy-16/S/-p-nitrobenzyloxycarbonylamido-17-phenyl-5-cis,13-trans-18,19,20-trinor-prostadienoic acid alkyl ester /isomer A/, and 9α,11α,15/ξ/-trihydroxy-16/S/-p-nitrobenzyloxycarbonylamido-17-phenyl-5-cis,13-trans-18,19,20-trinor-prostadienoic acid alkyl ester /isomer B/ derivatives are obtained.

Following the above reaction scheme, then applying the process of the invention, and starting from R-phenylalanine, 9α,11α,15/ξ/-trihydroxy-16/R/-amino-17-phenyl-5-cis,13-trans-18,19,20-trinor-prostadienoic acid /isomer A/, from /S/-p-chloro-phenylalanine 9α,11α,15/ξ/-trihydroxy-16/S/-amino-17-p-chlorophenyl-5-cis,13-trans-18,19,20-trinor-prostadienoic acid /isomer A/, from /S/-tyrosine 9α,11α,15/ξ/-trihydroxy-16/S/-amino-17-p-hydroxyphenyl-5-cis,13-trans-18,19,20-trinor-prostadienoic acid /isomer A/, from /S/-p-methylphenylalanine, 9α,11α,15/ξ/-trihydroxy-16/S/-amino-17-p-methylphenyl-5-cis,13-trans-18,19,20-trinor-prostadienoic acid /isomer A/, and from /S/-p-methoxy-phenylalanine 9α,11α,15/ξ/-trihydroxy-16/S/-amino-17-p-methoxyphenyl-5-cis,13-trans-18,19,20-trinor-prostadienoic acid /isomer A/, as well as the respective lower alkyl esters of the above compounds were prepared.

Submitting the 9α,11α,15/ξ/-trihydroxy-16-amino-17-phenyl-5-cis,13-trans-18,19,20-trinor-prostadienoic acid derivatives to tests developed for characterizing the biological effects of $PGF_{2\alpha}$, it was revealed, that their therapeutic effect is superior to that of $PGF_{2\alpha}$, $PGF_{2\alpha}$ and its several derivatives were introduced into therapy and the obstetric practice about 10 years ago. Recently they are applied in the veterinary practice for estrus-synchronizing. The abortion inducing effect of these compounds was investigated in various experimental conditions on several species.

According to one of the test methods /M. J. K. Harper and R. C. Skarnes: Advances in Biosciences 9, 789 /1973// the test material was administered subcutaneously to mice being in the 16th to 17th day of their pregnancy /3rd trimestre/, then the number of abortions ensuing with 48 hours was registered, as well as the live and dead fetuses following the removal of the uterus, and the scars on the placenta.

Another study reveals the effect on the early phase of pregnancy. Here hamsters being in the 4th, 5th, and 6th day of pregnancy were treated subcutaneously, and following autopsy on the 8th day, the number of intrauterine embryonal implantations, as well as the condition of the ovaria were investigated /N. S. Crossley: Prostaglandins 10, 5 /1975//. Similarly rats were treated on the 4th, 5th, 6th and 7th day of pregnancy, and killed on the 9th day, and the interruption of pregnancy registered at the autopsy /W. Skuballa et al.: J. Med. Chem. 2, 443 /1978//.

Applying the above methods the dose-response relationship was established at $PGF_{2\alpha}$, and its methyl ester, as well as the compounds of general formula I of the present invention. The number of animals was 5 per dose.

Taking 9α,11α,15/ξ/-trihydroxy-16/S/-amino-17-phenyl-5-cis,13-trans-18,19,20-prostadienoic acid methyl ester /isomer A/ as an example, the results obtained on pregnant mice are represented in the next table.

| Compound | Approx. $ED_{50}$ mg/kg body weight |
|---|---|
| $PGF_{2\alpha}$ | 16 |
| $PGF_{2\alpha}$-methyl ester | 10 |
| 9α,11α,15/ξ/-Trihydroxy-16/S/-amino-17-phenyl-5-cis,13-trans-18,19,20-trinor-prostadienoic acid methyl ester /isomer A/ | 1.2 |

According to the $ED_{50}$ values /dose inducing abortion in 50 percent of the animals/, obtained by interpolation, it is apparent that the new compound exhibits a 13 fold potency compared to $PGF_{2\alpha}$, and an 8 fold potency compared to $PGF_{2\alpha}$ methyl ester.

A similar increase in potency could be observed at the treatment of animals being in the 1st trimestre of their pregnancy.

| | Approx. $ED_{50}$ μg/kg body weight | |
|---|---|---|
| Compound | hamster | rat |
| $PGF_{2\alpha}$ | 25 | 1000 |
| 9α,11α,15/ξ/-Trihydroxy-16/S/-amino-17-phenyl-5-cis,13-trans-18,19,20,trinor-prostadienoic acid methyl ester /isomer A/ | 0.5 | 100 |

The 50 fold increase in potency compared to that of $PGF_{2\alpha}$ is especially worth mentioning in the case of hamsters, as this test is suitable for the sensitive detection of the abortive effect of a given compound if it has lutheolytic activity.

According to our investigations the 9α,11α,15/ξ/-trihydroxy-16-amino-17-phenyl-5-cis,13-trans-18,19,20-trinor-prostadienoic acid derivatives have no adverse effect on the functioning of the intestinal tract of the experimental animals, unlike the natural prostaglandins. At a dosis of 10 mg of $PGF_{2\alpha}$/kg and 3 mg of $PGF_{2\alpha}$-methyl ester/kg the incidence of diarrhoea was over 50 percent in pregnant mice, while 9α,11α,15/ξ/-trihydroxy-16/S/-amino-17-phenyl-5-cis,13-trans-18,19,20-trinor-prostadienoic acid methyl ester /isomer A/ failed to induce diarrhoea in a dosis of 3 mg/kg. This dose is 2.5 fold of that which causes abortion in 50 percent of the pregnant animals.

The investigations carried out on isolated organs showed similar effects to those which were achieved in vivo. Studying the effective concentrations of the compound on the smooth muscle, organs were suspended in isotonic salt solution in a constant oxygen flow. It was found that the ileum of the mouse, rat and guinea pig, furthermore the bronchial and uterine muscles of the guinea pig are relatively insensitive to the new derivatives. In agreement with this the minimal dose inducing uterus contraction in the mouse, hamster and rat is larger by 1 to 2 orders of magnitude than in the case of PGF$_{2\alpha}$.

Consequently, contrary to PGF$_{2\alpha}$, the abortive efficiency of the new derivatives is not due to their effect exerted directly on the smooth muscle.

The metabolic stability of the new derivatives is also playing a major role in the excellent biological potency of the compounds: prostaglandin-15-hydroxy-dehydrogenase, isolated from the lung, and being the most active inactivating enzyme of natural prostaglandins, fails to oxidize the 16-amino-17-phenyl-18,19,20-trinor-prostaglandin derivatives. Furthermore the new derivatives do not inhibit the enzymatic oxidation of PGF$_{2\alpha}$ either /test system: P. Tolnay et al.: Acta Biochim. Biophys. Acad. Sci. Hung. 14, 67 /1979//.

The 9α,11α,15/ξ/-trihydroxy-16-amino-17-phenyl-5-cis,13-trans-18,19,20-trinor-prostadienic acid derivatives of the invention can be converted into pharmaceutical compositions by usual methods applied in drug processing /it is especially advantageous to prepare injections/. These formulations may find application primarily in cattle raising for estrus and birth synchronization, furthermore in the veterinary praxis for the treatment of sterility, chronic endometritis, or pyometry.

The single dose of a compound of the invention, calculated for various animals species, amounts to 2.0 mg/animal in the case of cows, 1.0 mg/animal in the case of horses, and 2.0 mg/animal in the case of pigs, each administered intramuscularly.

The invention is further illustrated by but not limited to the following Examples.

EXAMPLE 1

9α,11α,15/ξ/-Trihydroxy-16/S/-amino-17-phenyl-5-cis,13-trans-18,19,20-trinor-prostadienoic acid methyl ester /I; Y=CH$_3$, W=H, isomer A/

9α,11α,15/ξ/-Trihydroxy-16/S/-p-nitrobenzyloxycarbonylamido-17-phenyl-5-cis,13-trans-18,19,20-trinor-prostadienoic acid methyl ester isomer A/ /1.2 g, 0.002 mole/ is dissolved in acetic acid /18 ml/, then water /6 ml/ and Zn dust /650 mg/ is added to the solution cooled to 0° C., at constant stirring. The reaction mixture is stirred for 1 hour at 0° C. under nitrogen, then its pH is adjusted with a solution of 2 N sodium hydroxide to 6 at cooling, and is freeze-dried. The solid residue is submitted to chromatography on a column prepared from silica gel /30 g, Kieselgel 40, Reanal, Budapest/ in chloroform-methanol mixtures containing gradually increasing amounts of methanol. The product itself is eluted from the column with a mixture containing 14 percent of methanol. Yield: 650 mg /77 percent/ of a chromatographically pure /thin-layer chromatography, developing solvent: methanol-chloroform 30:70, R$_F$=0.6/ 9α,11α,15/ξ/-trihydroxy-16/S/-amino-17-phenyl-5-cis,13-trans-18,19,20-trinor-prostadienoic acid methyl ester /isomer A/. IR spectrum /film/: νOH 3700-3200, νC=1720, γCH=CH /trans/ 970 cm$^{-1}$.
NMR spectrum /DMSO-d$_6$/: δ2.8 /H-16, m, 1H/, 3.6 /OCH$_3$, s, 3H/, 3.8-4.3 /H-9,11,15, m, 3H/, 5.4 /H-5,6, m, 2H/, 5.6-5.8 /H-13,14, m, 2H/, 7.35 /H-Ar, s, 5H/ ppm.

Mass spectrum: MW /m/z/: 417.

Mass number of characteristic ions /m/z/: 417, 386, 326, 120, 91. The hydrochloride of the aimed product: oil, Cl-content: 7,69% /measured/.

EXAMPLE 2

9α,11α,15/ξ/-Trihydroxy-16/S/-amino-17-phenyl-5-cis,13-trans-18,19,20-trinor-prostadienoic acid methyl ester /I; Y=CH$_3$, W=H, isomer B/

9α,11α,15/ξ/-Trihydroxy-16/S/-p-nitrobenzyloxycarbonylamido-17-phenyl-5-cis,13-trans-18,19,20-trinor-prostadienoic acid methyl ester /isomer B/ /750 mg, 0.0013 mole/ is dissolved in acetic acid /12 ml/, then water /4 ml/ and Zn dust /410 mg/ are added to the solution cooled to 0° C. at constant stirring. The reaction mixture is stirred at 0° C. under nitrogen for 1 hour, then the product is isolated according to the procedure described in Example 1. Yield: 380 mg /72 percent/ of 9α,11α,15/ξ/-trihydroxy-16/S/-amino-17-phenyl-5-cis,13-trans-18,19,20-trinor-prostadienoic acid methyl ester /isomer B/.

IR spectrum /film/: νOH 3700-3200, νC=O 1720, γCH=CH /trans/ 970 cm$^{-1}$.

NMR spectrum /DMSO-d$_6$/: δ3.0 /H-16, m, 1H/, 3.6 /OCH$_3$, s, 3H/, 3.74-4.3 /H-9,11,15, m, 3H/, 5.4 /H-5,6, m, 2H/, 5.6-5.8 /H-13,14, m, 2H/, 7.3 /H-Ar, s, 5H/ ppm.

Mass spectrum: MW /m/z/: 417.

Mass number of characteristic ions /m/z/: 417, 386, 326, 120, 91.

The starting materials of Examples 1 and 2 can be prepared according to the following process:

a./

9α,11α-Diacetoxy-15-oxo-16/S/-p-nitrobenzyloxycarbonylamido-17-phenyl-5-cis,13-trans-18,19,20-trinor-prostadienoic acid methyl ester /X; X=Y=CH$_3$, W=H/ p-Nitrobenzyloxycarbonyl-S-phenylalanine /8.6 g, 0.025 mole/ is dissolved in tetrahydrofuran /130 ml/, and at −15° C. N-methylmorpholine /2.7 ml, 0.025 mole/ and isobutyl chloroformate /3.2 ml, 0.025 mole/ are added to the solution. The mixture is stirred at −15° C. for 30 minutes, then a 2 percent ethereal solution of diazomethane /130 ml, 0.062 mole/ is added dropwise to the mixed anhydride obtained. The reaction mixture is stirred for further 2 hours at −15° C., then dry hydrogen chloride is led into the solution of the diazoketone derivative formed for 20 minutes. Subsequently the mixture is poured over ice-water /150 ml/, the organic layer washed three times with water /50 ml/ until it is HCl-free, then is dried over anhydrous sodium sulfate and evaporated at reduced pressure. N-pentane /30 ml/ is poured over the oily residue and the crystals formed filtered and dried at reduced pressure. The product obtained is homogeneous in thin layer chromatography /developing solvent: ethyl acetate-n-heptane 1:1, R$_F$=0.71/. Yield: 8.4 g /90 percent/ of 1-chloro-2-oxo-3/S/-p-nitrobenzyloxycarbonylamido-4-phenyl-butane, m.p. 106° to 110° C. [α]$_D$=+35.0 c=1, chloroform/.

IR spectrum /KBr/: νNH 3300, νC=O /ketone/ 1745, νC=O /amide/ 1700 cm$^{-1}$.

NMR spectrum /CDCl$_3$/: δ3.1 /CH$_2$-Ar, m, 2H/, 4.08 /CH$_2$Cl, q, 2H/, 4.7 /CH-NH, m, 1H/, 5.15 /CH$_2$-Ar-NO$_2$, s, 2H/, 5.4 /NH, m, 1H/, 7.3 /H-Ar, m, 5H/, 7.4, 8.3 /H-Ar-NO$_2$, 2xd, 4H/ ppm.

Tri-n-butylphosphine /5.4 ml, 0.022 mole/ is added under stirring to a solution of 1-chloro-2-oxo-3/S/-p-nitrobenzyloxycarbonylamido-4-phenyl-butane /7.5 g, 0.02 mole/ in dichloromethane /100 ml/. The reaction mixture is heated to 60° C. for 2 hours, then is evaporated to dryness under reduced pressure. Water /50 ml/ is poured over the residue, and the unreacted tri-n-butylphosphine is extracted three times with n-heptane /20 ml/. Diethylether /20 ml/ is added to the aqueous layer containing the tri-n-butyl-2-oxo-3/S/-p-nitrobenzyloxycarbonylamido-4-phenyl-butyl-phosphonium chloride, and 2 N sodium hydroxide is added dropwise /10 ml/ under cooling /5° C./, then the reaction mixture is stirred for 6 minutes. Then the aqueous layer is separated and extracted with ether /20 ml/. The combined ethereal extracts are dried over Klinosorb-4 /Reanal, Budapest/. This solution of tri-n-butyl-2-oxo-3/S/-p-nitrobenzyloxycarbonylamido-4-phenyl-butylidenephosphorane in ether is added at stirring, 5° C., and under nitrogen to a solution of 1α-/6-carbomethoxy-2-hexenyl/-2β-formyl-cyclopentane-3α,5α-diol-diacetate /3.5 g, 0.01 mole/ in ether /5 ml/. The reaction mixture is stirred for 7 hours at 5° C., then the solvent is evaporated at reduced pressure. The residue is submitted to chromatography on a silicic acid column /150 g/ with a solvent system of n-hexane-ethyl acetate containing gradually increasing amounts of ethyl acetate. The product is eluted from the column with a mixture containing 14 percent of ethyl acetate. Yield: 5 g 75 percent/ of 9α,11α-diacetoxy-15-oxo-16/S/-p-nitrobenzyloxycarbonylamido-17-phenyl-5-cis,13-trans-18,19,20-trinor-prostadienoic acid methyl ester /oil/.

IR spectrum /film/: $\nu$NH 3300, $\nu$C=O 1730 cm$^{-1}$.

NMR spectrum /CDCl$_3$/: $\delta$2.0 /CH$_3$CO, s, 2x3H/, 3.60 /OCH$_3$, s, 3H/, 4.8-5.2 /H-9,11,16, CH$_2$-Ar-NO$_2$, m, 5H, overlapping signals/, 5.2-5.5 /H-5,6, m, 2H, 6.1 /H-14, d, 1H/, 6.7 /H-13, 2xd, 1H/, 7.1 /H-Ar, m, 5H/, 7.3, 8.0 /H-Ar-NO$_2$, 2xd, 4H/ ppm.

Mass spectrum: MW: /m/z/: 678.

Mass number of characteristic ions /m/z/: 678, 587, 422, 405, 379, 337, 319, 299, 259.

b./

9α,11α-Diacetoxy-15/ξ/-hydroxy-16/S/-p-nitrobenzyloxycarbonylamido-17phenyl-5-cis,13-trans-18,19,20-trinor-prostadienoic acid methyl ester /isomer A/ and 9α,11α-diacetoxy-15/ξ/-hydroxy-16/S/-p-nitrobenzyloxycarbonylamido-17-phenyl-5-cis,13-trans-18,19,20-trinor-prostadienoic acid methyl ester /isomer B/ /XI; X=CH$_3$, Y=CH$_3$, W=H/

Sodium borohydride /265 mg, 0.007 mole/ is added at 5° C. and under stirring to a solution of 9α,11α-diacetoxy-15-oxo-16/S/-p-nitrobenzyloxycarbonylamido-17-phenyl-5-cis,13-trans-18,19,20-trinor-prostadienoic acid methyl ester 4.8 g, 0.007 mole/ in anhydrous methanol /80 ml/. The reaction mixture is stirred at 5° C. under nitrogen for one hour, then poured into a 0.2 mole sodium dihydrogen phosphate solution /300 ml/, cooled to 5° C. and extracted twice with ethyl acetate /100 ml/. The combined ethyl acetate extracts are dried over anhydrous sodium sulfate, and evaporated at reduced pressure. The crude product obtained is purified by preparative thin-layer chromatography, applying silica gel as adsorbent, and a mixture of ethyl acetate-n-heptane 1:1 as developing solvent. Yield: 2.4 g of 9α,11α-diacetoxy-15/ξ/-hydroxy-16/S/-p-nitrobenzyloxycarbonylamido-17-phenyl-5-cis,13-trans-18,19,20-trinor-prostadienoic acid methyl ester /polar product, isomer A, $R_F$=0.25/, and 1.5 g of 9α,11α-diacetoxy-15/ξ/-hydroxy-16/S/-p-nitrobenzyloxycarbonylamido-17-phenyl-5-cis,13-trans-18,19,20-trinor-prostadienoic acid methyl ester /apolar product, isomer B, $R_F$=0.36/. 9α,11α-Diacetoxy-15/ξ/-hydroxy-16/S/-p-nitrobenzyloxycarbonylamido-17-phenyl-5-cis,13-trans-18,19,20-trinor-prostadienoic acid methyl ester /isomer A/: M.p.: 71°-73° C.

IR spectrum /film/: $\nu$OH 3600-3300, $\nu$C=O 1730 (broad), c=c 1615, $\gamma$C=C /trans/ 970 cm$^{-1}$.

NMR spectrum /CDCl$_3$/: $\delta$2.0, 2.1 /CH$_3$CO, s, 2x3H/, 3.6 /OCH$_3$, s 3H/, 3.8-4.3 /H-15,16, m, 2H/, 4.8-5.2 /H-9,11, m, CH$_2$-Ar-NO$_2$, 4H/, 5.3 /H-5,6, m, 2H/, 5.6 /H-13,14, m, 2H/, 7.2 /H-Ar, m, 5H/, 7.3, 8.1 /H-Ar-NO$_2$, 2xd, 4H/ ppm.

Mass spectrum:

Mass number of characteristic ions /m/z/: 589, 452, 436, 392, 391, 299, 272, 255, 136.

9α,11α-Diacetoxy-15/ξ/-hydroxy-16/S/-p-nitrobenzyloxycarbonylamido-17-phenyl-5-cis,13-trans-18,19,20-trinor-prostadienoic acid methyl ester /isomer B/. M.p.: 81°-83° C.

IR spectrum /film/: $\nu$OH 3600-3300, $\nu$C=O 1730 (broad), $\nu$C=C 1615, $\gamma$CH=CH /trans/ 970 cm$^{-1}$.

NMR spectrum /CDCl$_3$/: $\delta$2.0, 2.1 /CH$_3$CO, s, 2x3H/, 3.6 /OCH$_3$, s, 3H/, 3.8-4.3 /H-15,16, m, 2H/, 4.8-5.2 /H-9,11, CH$_2$-Ar-NO$_2$ m, 4H/, 5.3 /H-5,6, m, 2H/, 5.6 /H-13,14, m, 2H/, 7.2 /H-Ar, m, 5H/, 7.3, 8.1 /H-Ar-NO$_2$, 2xd, 4H/ ppm.

Mass spectrum:

Mass number of characteristic ions /m/z/: 589, 452, 436, 392, 381, 299, 255, 136.

c$_1$./

9α,11α,15/ξ/-Trihydroxy-16/S/-p-nitrobenzyloxycarbonylamido-17-phenyl-5-cis,13-trans-18,19,20-trinor-prostadienoic acid methyl ester /XII; Y=CH$_3$, W=H, isomer A/

9α,11α-Diaeetoxy-15/ξ/-hydroxy-16/S/-p-nitrobenzyloxycarbonylamido-17-phenyl-5-cis,13-trans-18,19,20-trinor-prostadienoic acid methyl ester /isomer A/ /2 g, 0.003 mole/ is dissolved in anhydrous methanol /150 ml/ and p-toluenesulfonic acid /4.6 g, 0.024 mole/ is added to the solution. The reaction mixture is stirred under nitrogen at room temperature for 36 hours, then it is poured into a 1 M solution of disodium hydrogen phosphate /210 ml/ /pH 6/, and extracted three times with ethyl acetate /100 ml/. The combined ethyl acetate extracts are evaporated at reduced pressure, and the residue submitted to chromatography applying silica gel as adsorbent /100 g, Kieselgel 40, Reanal, Budapest/, and a mixture of n-hexane-ethyl acetate, containing gradually increasing amounts of ethyl acetate, as developing solvent. The product itself is eluted from the column with a solvent mixture containing 10 percent of n-hexane in ethyl acetate. Yield: 1.3 g /75 percent/ of homogeneous 9α,11α,15/ξ/-trihydroxy-16/S/-p-nitrobenzyloxycarbonylamido-17-phenyl-5-cis,13-trans-18,19,20-trinor-prostadienoic acid methyl ester /isomer A/.

M.p.: 76°-78° C.

IR spectrum /film/: $\nu$OH+NH 3600-3100, $\nu$C=O 1710, $\nu$C=C 1610 cm$^{-1}$.

NMR spectrum /CDCl$_3$/: $\delta$3.6 /OCH$_3$, s, 3H/, 3.9 /H-15,16, m, 2H/, 4.1 /H-9,11, m, 2H/, 5.2 /CH$_2$-Ar-NO$_2$, overlapping signals/, 5.3 /H-5,6, m, 2H/, 5.5 /H-13,14, m, 2H/, 7.3 /H-Ar, H-Ar-NO$_2$, overlapping signals/, 8.1 /H-Ar/o-nitro/, d, 2H/ ppm.

Mass spectrum:

Mass number of characteristic ions /m/z/: 399, 368, 352, 308, 299, 290, 236, 91.

c$_2$./
9α,11α,15/ξ/-Trihydroxy-16/S/-p-nitrobenzyloxycarbonylamido-17-phenyl-5-cis,13-trans-18,19,20-trinor-prostadienoic acid methyl ester /XII; Y=CH$_3$, W=H, isomer B/

9α,11α-Diacetoxy-15/ξ/-hydroxy-16/S/-p-nitrobenzyloxycarbonylamido-17-phenyl-5-cis,13-trans-18,19,20-trinor-prostadienoic acid methyl ester /isomer B/ /1.04 g, 0.002 mole/ is dissolved in anhydrous methanol /100 ml/ and p-toluenesulfonic acid /3 g, 0.016 mole/ added to it. The reaction mixture is stirred under nitrogen for 36 hours at room temperature, and the product formed isolated according to the procedure described in /c$_1$./. Yield: 850 mg /70 percent/ of pure 9α,11α,15/ξ/-trihydroxy-16/S/-p-nitro-benzyloxycarbonylamido-17-phenyl-5-cis,13-trans-18,19,20-trinor-prostadienoic acid methyl ester /isomer B/.

M.p.: 69°–71° C.

IR spectrum /film/: $\nu$NH+OH 3600–3100, $\nu$C=O 1730, $\nu$C=C 1615 cm$^{-1}$.

NMR spectrum /CDCl$_3$/: δ3.6 /OCH$_3$, s, 3H/, 3.8 /H-15,16, m, 2H/, 4.1 /H-9,11, m, 2H/, 5.0 /CH$_2$-Ar-NO$_2$, overlapping signals/, 5.3 /H-5,6, m, 2H/, 5.5 /H-13,14, m, 2H/, 7.3, 7.4 /H-Ar, H-Ar-NO$_2$, overlapping signals/, 8.1 /H-Ar/o-nitro/, d, 2H/ ppm.

Mass spectrum:
Mass number of characteristic ions /m/z/: 399, 368, 352, 308, 299, 290, 255, 236.

EXAMPLE 3

9α,11α,15/ξ/-Trihydroxy-16/S/-amino-17-phenyl-5-cis,13-trans-18,19,20-trinor-prostadienoic acid /I; Y=W=H, isomer A/

Lithium hydroxide /500 mg, 0.021 mole/, dissolved in water /8 ml/, is added at 0° C. to a solution of 9α,11α,15/ξ/-trihydroxy-16/S/-amino-17-phenyl-5-cis,13-trans-18,19,20-trinor-prostadoenoic acid methyl ester /isomer A, Example 1/ /600 mg, 0.0014 mole/ in methanol. The reaction mixture is stirred under nitrogen at 0° C. for 16 hours, then the pH of the solution is adjusted with 8 percent aqueous oxalic acid solution to 5.5. The methanol is evaporated at reduced pressure and 5° C., and the residual aqueous solution freeze-dried. The dry residue is submitted to chromatography on a silica gel column /10 g/, Kieselgel 40, Reanal, Budapest/ with a solvent system of chloroform-methanol, containing gradually increasing amounts of methanol. The product is eluted from the column with chloroform containing 20 percent of methanol. Yield: 500 mg /86 percent/ of 9α,11α,15/ξ/-trihydroxy-16/S/-amino-17-phenyl-5-cis,13-trans-18,19,20-trinor-prostadienoic acid /isomer A/ /homogeneous in thin-layer chromatography, applying methanol-chloroform 30:70 as developing solvent, R$_F$=0.25/.

IR spectrum /film/: $\nu$OH 3700–2500, $\nu$COOH 1700 /shoulder/, $\nu$COO$^-$ 1560, γCH=CH /trans/ 970 cm$^{-1}$. NMR spectrum /DMSO-d$_6$/: δ2.8 /H-16, m, 1H/, 3.8, 4.0, 4.25 H-9,11,15, m, 3H/, 5.35 /H-5,6, m, 2H/, 5,5–5,6 /H-13,14, m, 2H/, 7,35 /H-Ar, s, 5H/ ppm.

EXAMPLE 4

9α,11α,15/ξ/-Trihydroxy-16/S/-amino-17-phenyl-5-cis,13-trans-18,19,20-trinor-prostadienoic acid /I; Y=W=H, isomer B/

Lithium hydroxide /270 mg, 0.0112 mole/, dissolved in water /4 ml/, is added at 0° C. to a solution of 9α,11α,15/ξ/-trihydroxy-16/S/-amino-17-phenyl-5-cis,13-trans-18,19,20-trinor-prostadienoic acid methyl ester /isomer B, Example 2/ /315 mg, 0.00075 mole/ in methanol /12 ml/. The reaction mixture is stirred under nitrogen at 0° C. for 16 hours, then the product is isolated according to the procedure described in Example 3. Yield: 280 mg /90 percent/ of chromatographycally pure 9α,11α,15/ξ/-trihydroxy-16/S/-amino-17-phenyl-5-cis,13-trans-18,19,20-trinor-prostadienoic acid /isomer B/.

IR spectrum /film/: $\nu$OH 3700–2500, $\nu$COOH 1700, $\nu$COO$^-$ 1570, γCH=CH /trans/ 970 cm$^{-1}$.

NMR spectrum /DMSO-d$_6$/: δ2,9 /H-16, m, 1H/, 3.5–4,2 /H-9,11,15, m, 3H/, 5.4 /H-5,6, m, 2H/, 5.5–5.6 /H-13,14, m, 2H/, 7.3 /H-Ar, s, 5H/ ppm.

EXAMPLE 5

9α,11α,15/ξ/-Trihydroxy-16/S/-amino-17-p-hydroxyphenyl-5-cis,13-trans-18,19,20-trinor-prostadienoic acid methyl ester /I; Y=CH$_3$, W=OH, isomer A/

9α,11α,15/ξ/-Trihydroxy-16/S/-p-nitrobenzyloxycarbonylamido-17-p-hydroxyphenyl-5-cis,13-trans-18,19,20-trinor-prostadienoic acid methyl ester /isomer A/ /612 mg, 0,001 mole/ is dissolved in acetic acid /9 ml/, and at 0° C. and stirring water /3 ml/ and Zn dust /325 mg/ are added to the solution. The reaction mixture is stirred under nitrogen at 0° C. for 1 hour, then the pH of the solution is adjusted with a solution of sodium hydroxide /2 N/ to 6, at cooling, and the solution is freeze-dried. The solid residue is submitted to chromatography on a silica gel column /10 g, Kieselgel 40, Reanal, Budapest/, with a mixture of chloroform-methanol, containing gradually increasing amounts of methanol. The product is eluted from the column with chloroform containing 12 percent of methanol. Yield: 340 mg /78 percent/ of 9α,11α,15/ξ/-trihydroxy-16/S/-amino-17-p-hydroxyphenyl-5-cis,13-trans-18,19,20-trinor-prostadienoic acid methyl ester /isomer A/, homogeneous in thin-layer chromatography.

IR spectrum /film/: $\nu$OH 3600–3100, $\nu$C=O 1725 cm$^{-1}$.

NMR spectrum /CD$_3$OD/: δ2,7 /H-16, m, 1H/, 3.6 /OCH$_3$, s, 3H/, 3.9–4.3 /H-9,11,15, m, 3H/, 5.4 /H-5,6, m, 2H/, 5.6 /H-13,14, m, 2H/, 6.7 /H-Ar, d, 2H/, 7.1 /H-Ar, d, 2H/ ppm.

Mass spectrum: MW /m/z/: 433
Mass number of characteristic ions /m/z/: 433, 326, 310, 164, 150, 136.

EXAMPLE 6

9α,11α,15/ξ/-Trihydroxy-16/S/-amino-17-p-chlorophenyl-5-cis,13-trans-18,19,20-trinor-prostadienoic acid methyl ester /I; Y=CH$_3$, W=Cl, isomer A/

9α,11α,15/ξ/-Trihydroxy-16/S/-p-nitrobenzyloxycarbonylamido-17-p-chlorophenyl-5-cis,13-trans-18,19,20-trinor-prostadienoic acid methyl ester /isomer A/ /630 mg, 0.001 mole/ is dissolved in acetic acid /9 ml/, then water /3 ml/ and Zn dust /325 mg/ are added to the solution at 0° C. and constant stirring. The reaction mixture is stirred under nitrogen at 0° C. for 1 hour, then the pH of the solution is adjusted with a 2 N sodium hydroxide solution to 6, and freeze-dried. The solid residue is submitted to chromatography on a silica gel column /10 g, Kieselgel 40, Reanal, Budapest/ in a solvent system of chloroform-methanol, containing increasing amounts of methanol. The product is eluted from the column with chloroform containing 10 percent of methanol. Yield: 340 mg /72 percent/ of 9α,11α,15/ξ/-trihydroxy-16/S/-amino-17-p-chlorophenyl-5-cis,13-trans-18,19,20-trinor-prostadienoic acid methyl ester /isomer A/ /homogeneous according to thin-layer chromatography/.

IR spectrum /film/: νOH 3600–3100, νC=O 1730 cm⁻¹.

NMR spectrum /CD₃OD/: δ2.8 /H-16, m, 2H/, 3.1 /CH₂-Ar, m, 2H/, 3.6 /OCH₃, s, 3H/, 3.8–4.2 /H-9,11,15, m, 3H/, 5.4 /H-5,6, m, 2H/, 5.6 /H-13,14, m, 2H/, 7.2 /H-Ar, s, 4H/ ppm.

EXAMPLE 7

9α,11α,15/ξ/-Trihydroxy-16/S/-amino-17-phenyl-5-cis,13-trans-18,19,20-trinor-prostadienoic acid /I,Y=H, isomer A/

9α,11α,15/ξ/-Trihydroxy-16/S/-p-nitrobenzyl-oxycarbonylamido-17-phenyl-5-cis,13-trans-18,19,20-trinor-prostadienoic acid methyl ester /isomer A, 300 mg/, *Rhizopus oryzae* lipase enzyme /60 mg/, acacia gum /350 mg/ and sodium taurocholate /15 mg/ are added to a 0.1 M phosphate buffer /20 ml, pH 8/. The suspension is shaken on a rotary shaker at 28° C. for days, then diluted with water /100 ml/, acidified with citric acid to pH 3 and extracted three times with ethylacetate /20 ml/. The combined ethylacetate extracts are evaporated at reduced pressure. The residue, containing the 9α,11α,15/ξ/-trihydroxy-16/S/-p-nitrobenzyloxycarbonylamido-17-phenyl-5-cis,13-trans-18,19,20-trinor-prostadienoic acid /isomer A/, is dissolved in 70% aqueous acetic acid /5 ml/, cooled to 0° C., and stirred at this temperature under nitrogen for 1 hour with Zn dust /290 mg/. Then the reaction mixture is diluted with dichloromethane /20 ml/, the Zn dust filtered off, and the filtrate evaporated at reduced pressure. The residue is submitted to chromatography on a column prepared from silica gel /5 g/, in a system of chloroform-methanol containing gradually increasing amounts of methanol. The product itself is eluted from the column with a mixture containing 20% of methanol. Yield: 101 mg /50%/ of 9α,11α,15/ξ/-trihydroxy-16/S/-amino-17-phenyl-5-cis,13-trans-18,19,20-trinor-prostadienoic acid /isomer A/.

EXAMPLE 8

Preparation of A Pharmaceutical Composition

For veterinary purposes 5 ml injections containing 2 mg of the active substance are prepared according to the following:

| | |
|---|---|
| 9α11α,15/ /-trihydroxy-16/S/-amino-17-phenyl-5-cis,13-trans-18,19,20-trinor-prostadienoic acid methyl ester /isomer A/ | 2 mg |
| benzyl alcohol | 40 mg |
| propyleneglycol | 100 mg |
| distilled water | ad 5 ml |

What we claim is:
1. 16-Amino-18,19,20-trinor-prostaglandin derivatives of general formula I

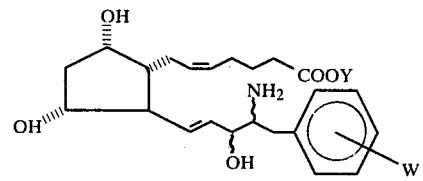

having at C-17 a substituted or unsubstituted phenyl group, wherein C-15 and C-16 may have either S or R configuration, Y stands for a hydrogen atom or a lower alkyl group, W for a hydrogen atom, halogen atom, hydroxy group, lower alkyl or alkoxy group, and their acid addition salts.

2. A compound as claimed in claim 1, wherein C-16 has S configuration.

3. 9α,11α,15/S/-Trihydroxy-16/S/-amino-17-phenyl-5-cis,13-trans-18,19,20-trinor-prostadienoic acid methyl ester or a pharmaceutically acceptable salt thereof.

4. 9α,11α,15/R/-Trihydroxy-16/S/-amino-17-phenyl-5-cis,13-trans-18,19,20-trinor-prostadienoic acid methyl ester or a pharmaceutically acceptable salt thereof.

5. 9α,11α,15/S/-Trihydroxy-16/S/-amino-17-phenyl-5-cis,13-trans-18,19,20-trinor-prostadienoic acid or a pharmaceutically acceptable salt thereof.

6. 9α,11α,15/R/-Trihydroxy-16/S/-amino-17-phenyl-5-cis,13-trans-18,19,20-trinor-prostadienoic acid or a pharmaceutically acceptable salt thereof.

7. 9α,11α,15/S/-Trihydroxy-16/S/-amino-17-p-chlorophenyl-5-cis,13-trans-18,19,20-trinor-prostadienoic acid methyl ester or a pharmaceutically acceptable salt thereof.

8. 9α,11α,15/R/-Trihydroxy-16/S/-amino-17-p-chlorophenyl-5-cis,13-trans-18,19,20-trinor-prostadienoic acid methyl ester or a pharmaceutically acceptable salt thereof.

9. 9α,11α,15/S/-Trihydroxy-16/S/-amino-17-p-chlorophenyl-5-cis,13-trans-18,19,20-trinor-prostadienoic acid or a pharmaceutically acceptable salt thereof.

10. 9α,11α,15/R/-Trihydroxy-16/S/-amino-17-p-chlorophenyl-5-cis,13-trans-18,19,20-trinor-prostadienoic acid or a pharmaceutically acceptable salt thereof.

11. A pharmaceutical composition for veterinary purposes, which comprises a pharmaceutically effective amount of a compound of general formula I, as defined in claim 1, or a pharmaceutically acceptable salt thereof.

* * * * *

UNITED STATES PATENT AND TRADEMARK OFFICE
CERTIFICATE OF CORRECTION

PATENT NO. : 4,418,205

DATED : November 29, 1983

INVENTOR(S) : Eva Toth-Sarudy; Grabor Ambrus; Gyorgy Cseh; Janos Borvendeg; Imre Moravcsik and Gabriella Mezei It is certified that error appears in the above-identified patent and that said Letters Patent is hereby corrected as shown below:

On the title page, correct line [73] to read as follows:

-- Gyogyszerkutato Intezet, Budapest, Hungary --.

Signed and Sealed this

Thirteenth Day of November 1984

[SEAL]

Attest:

GERALD J. MOSSINGHOFF

Attesting Officer   Commissioner of Patents and Trademarks